(12) United States Patent
Glaw (10) Patent No.: US 9,649,457 B2
(45) Date of Patent: May 16, 2017

(54) PROCESS FOR OPERATING A RESPIRATOR AND/OR ANESTHESIA DEVICE AND A DEVICE OPERATED CORRESPONDINGLY

(75) Inventor: Tobias Glaw, Lübeck (DE)

(73) Assignee: Drägerwerk AG & Co. KGaA, Lübeck (DE)

( * ) Notice: Subject to any disclaimer, the term of this patent is extended or adjusted under 35 U.S.C. 154(b) by 2193 days.

(21) Appl. No.: 12/101,287

(22) Filed: Apr. 11, 2008

(65) Prior Publication Data

US 2008/0295838 A1  Dec. 4, 2008

(30) Foreign Application Priority Data

Jun. 4, 2007  (DE) .......................... 10 2007 026 036

(51) Int. Cl.
*A61M 16/00* (2006.01)
*A61M 16/01* (2006.01)
*A61B 5/087* (2006.01)

(52) U.S. Cl.
CPC ........ *A61M 16/0051* (2013.01); *A61M 16/01* (2013.01); *A61B 5/0871* (2013.01); *A61M 2016/0021* (2013.01); *A61M 2016/0036* (2013.01)

(58) Field of Classification Search
CPC .......... A61M 16/0057; A61M 16/0063; A61M 16/0066; A61M 16/0069; A61M 16/01; A61M 16/0051; A61B 5/0871
USPC ............ 128/203.12, 204.18, 204.21, 204.23, 128/204.26
See application file for complete search history.

(56) References Cited

U.S. PATENT DOCUMENTS

| | | | | |
|---|---|---|---|---|
| 5,099,836 | A * | 3/1992 | Rowland et al. | 128/204.23 |
| 5,398,682 | A * | 3/1995 | Lynn | 600/335 |
| 6,752,151 | B2 * | 6/2004 | Hill | 128/204.18 |
| 2003/0111078 | A1 * | 6/2003 | Habashi | 128/204.18 |
| 2005/0005937 | A1 * | 1/2005 | Farrugia et al. | 128/204.18 |
| 2005/0224078 | A1 * | 10/2005 | Zdrojkowski et al. | 128/204.23 |
| 2006/0005834 | A1 * | 1/2006 | Aylsworth et al. | 128/204.21 |
| 2006/0174884 | A1 | 8/2006 | Habashi | |
| 2008/0078392 | A1 * | 4/2008 | Pelletier et al. | 128/204.23 |
| 2008/0283060 | A1 * | 11/2008 | Bassin | 128/204.18 |
| 2009/0020121 | A1 * | 1/2009 | Bassin | 128/204.23 |
| 2009/0293876 | A1 * | 12/2009 | Soliman et al. | 128/204.22 |

* cited by examiner

*Primary Examiner* — LaToya M Louis
(74) *Attorney, Agent, or Firm* — McGlew and Tuttle, P.C.

(57) ABSTRACT

A process for operating a respirator and/or an anesthesia device with measurement of a set percent Peak Expiratory Flow (% PEF) (15) or percent Peak Inspiratory Flow (% PIF) and regulation of the measured % PEF (15) or % PIF to the set % PEF (15) or % PIF. Furthermore, a suitable respirator and/or anesthesia device are provided.

14 Claims, 6 Drawing Sheets

PROCESS FOR OPERATING A RESPIRATOR AND/OR ANESTHESIA DEVICE AND A DEVICE OPERATED CORRESPONDINGLY

CROSS REFERENCE TO RELATED APPLICATIONS

This application claims the benefit of priority under 35 U.S.C. §119 of German Patent Application DE 10 2007 026 036.0 filed Jun. 4, 2007, the entire contents of which are incorporated herein by reference.

FIELD OF THE INVENTION

The present invention pertains to a process for operating a respirator (also known as a ventilator) and/or anesthesia device involving initiation of a respiration process at a first point in time, at which a measured respiratory flow reaches a percentage of a peak respiratory flow set on the device, the percent of set Peak Expiratory Flow (% PEFset)—Peak Expiratory Flow (% PEF) or percent Peak Inspiratory Flow (% PIF)—where at least one effect of the respiration process begins at a second point in time that is after the first point in time. The present invention pertains furthermore to an anesthesia device and/or respirator with a means for setting a percentage of a peak respiratory flow, a device for initiating a respiration process when the set percentage of the respiratory flow is reached, and a means for measuring the respiration flow.

BACKGROUND OF THE INVENTION

Figure 1A:
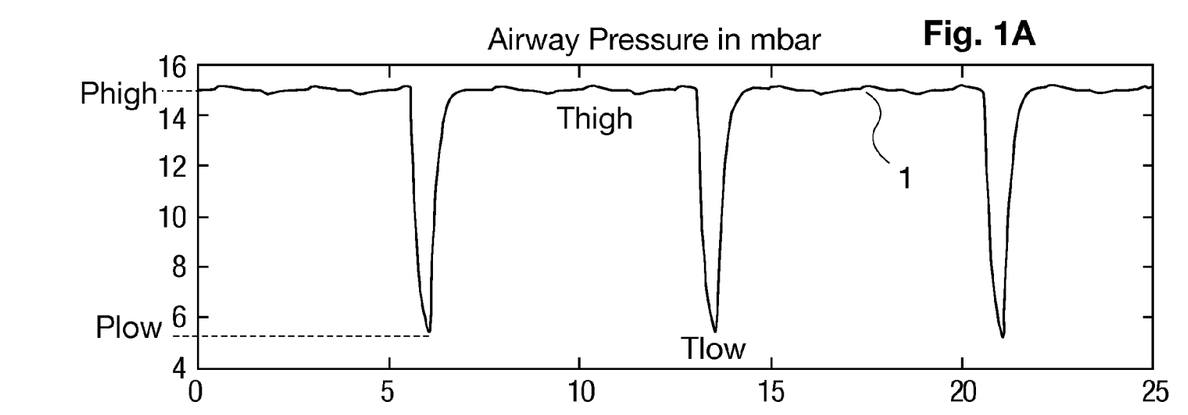
FIG. 1A is a pressure (in mbar) versus time (in seconds) graph showing a simulation of respiration in the APRV mode.
Figure 1B:
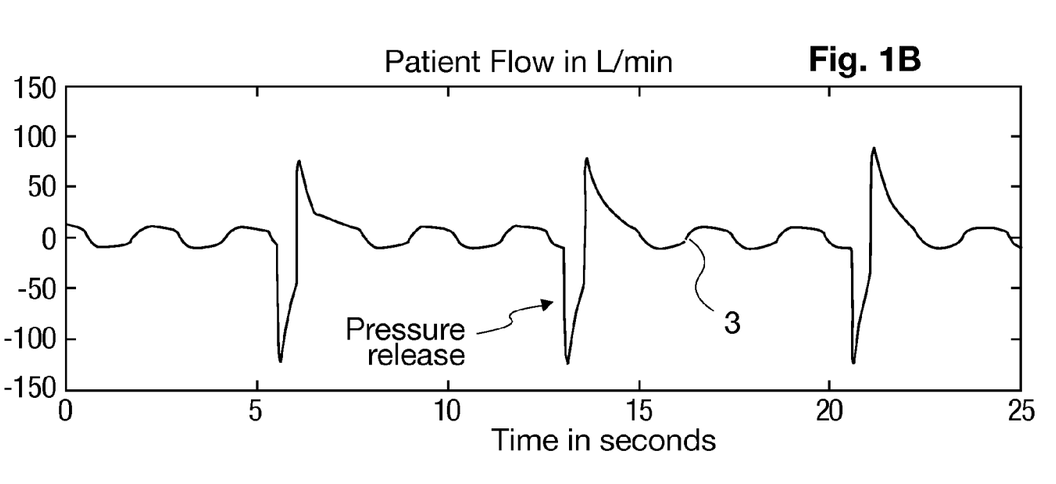
FIG. 1B is a patient flow (in L/min) versus time (in seconds) graph showing a simulation of a respiration in the APRV mode.

A respiration mode APRV (Airway Pressure Release Ventilation), which is, similarly to the CPAP mode, a mode with a continuous positive airway pressure (CPAP), is known from practice. Contrary to the CPAP respiration mode, an upper pressure $P_{high}$ is applied in the APRV mode. This pressure $P_{high}$ is regularly lowered for a short period of time to a lower pressure level $P_{low}$ this pressure reduction being called "pressure release." The patient being respirated by means of APRV can breathe spontaneously at any time, but synchronization of the pressure release with the respiratory activity of the patient is not performed. It is typical of the APRV mode that a duration $T_{high}$, during which the pressure $P_{high}$ is applied, is usually longer than a duration $T_{low}$, during which the lower pressure $P_{low}$ is present. FIG. 1 shows an example of respiration in the APRV mode in a simulation.

During respiration in the APRV mode, the mean respiration pressure is maintained at a comparatively high level, which leads to improved oxygenation. The elimination of $CO_2$ is supported by the pressure release. Due to the short duration $T_{low}$ and the short duration of the pressure release, removal of air from the lungs to the extent that alveoli could collapse and could not participate in the ventilation any longer is prevented from occurring. The duration $T_{low}$ is set such that complete breathing out is prevented from occurring. It can be recognized from FIG. 1B that the pressure release is terminated before the patient flow has risen to 0 L/minute (see the times t=5.5 sec; t=13 sec; t=21.5 sec in FIG. 1B).

A new set value for APRV ventilation, which is circumscribed as "optimal flow termination based on a percentage of peak expiratory flow," is proposed in the patent application US 2006/0174884 A1 of Nader M. Habashi. This set value will hereinafter be called % PEF (Peak Expiratory Flow). The parameter % PEF is set in percentage of a maximum expiratory flow or Peak Expiratory Flow (PEF). The pressure release is terminated when the instantaneous expiratory flow of the patient relative to the maximum expiration flow has dropped below the percentage set as % PEF (see for example FIG. 3). As a result, the algorithm automatically adapts the duration of pressure release to changes in the lungs. According to the above-mentioned US 2006/0174884 A1, the end of the duration $T_{low}$ shall be placed at the moment at which % PEF, which may be in a setting range between 25% and 50% of PEF (maximum expiratory flow), reaches or equals the set % PEF value. The expiratory gas flow is monitored for this purpose, PEF is determined, and the pressure release phase is interrupted when the expiratory gas flow drops below the preset percentage value % PEF.

If we assume in an example that % PEF is set at 50%, the pressure release is terminated in the APRV mode when the measured expiratory patient flow has dropped to 50% of the maximum value thereof. The expiration valve must be closed and an inspiration flow must be applied at this moment in order to achieve a pressure rise in the respiration system. However, it is known from practice that a valve always closes or opens with a time delay. In addition, system delays can be observed during the processing and transmission of information, e.g., a signal to the expiration valve, which indicates that the actual value has dropped below the set % PEF value. These delays lead, in their sum, to the lungs being able to be emptied further during the time that is due to these delays. The actual closing value of the expiration valve could thus be markedly below this value in the case in which the set value is 50% of % PEF. Likewise, when % PEF is set at 25%, a real closing value can be markedly below this 25%. However, since any random emptying is not allowed to take place for the above-mentioned reasons, the use of this % PEF criterion or parameter implies health hazards for the patient being respirated.

SUMMARY OF THE INVENTION

The object of the present invention is to provide a process for operating a respirator and/or anesthesia device, by means of which an actually present percentage of a peak respiratory flow can be determined and a corresponding regulation can be performed based on this in order to cause the determined percentage and a set percentage to agree with one another. Another goal of the present invention is to provide a suitable respirator and/or anesthesia device.

The object according to the present invention is accomplished by a process for operating a respirator and/or anesthesia device (hereinafter called respirator for short), in which a respiration process is initiated at a first point in time, at which a measured respiratory flow reaches a percentage of a peak respiratory flow set on the respirator, but the effect of this respiration process, e.g., a pressure rise when the respiration process is an inspiration process, begins at the second point in time only after the end of a time difference between the first point in time and a second point in time.

The respiration process, which is initiated at the first point in time, may be a machine-supported inspiratory respiration stroke, as it is common in pressure support (PS) or proportional pressure support (PPS). However, the respiration process may also be an expiratory process; in particular, it may represent an inspiratory respiration process taking place after interruption of the pressure release during respiration in the APRV mode and interruption of an inspiration process in the pressure support mode. Initiation of a respiration process is defined quite generally in the sense of the present invention as a transition during respiration from a first phase of respiration into a second phase of respiration, which is different therefrom.

Figure 2A:
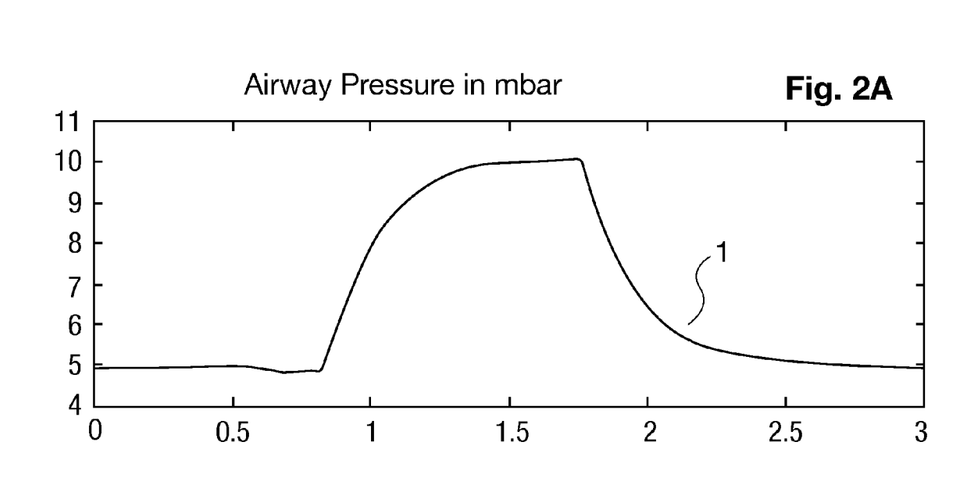
FIG. 2A is a pressure (in mbar) versus time (in seconds) graph showing an example of respiration with respiration strokes supported during the inspiration.
Figure 2B:
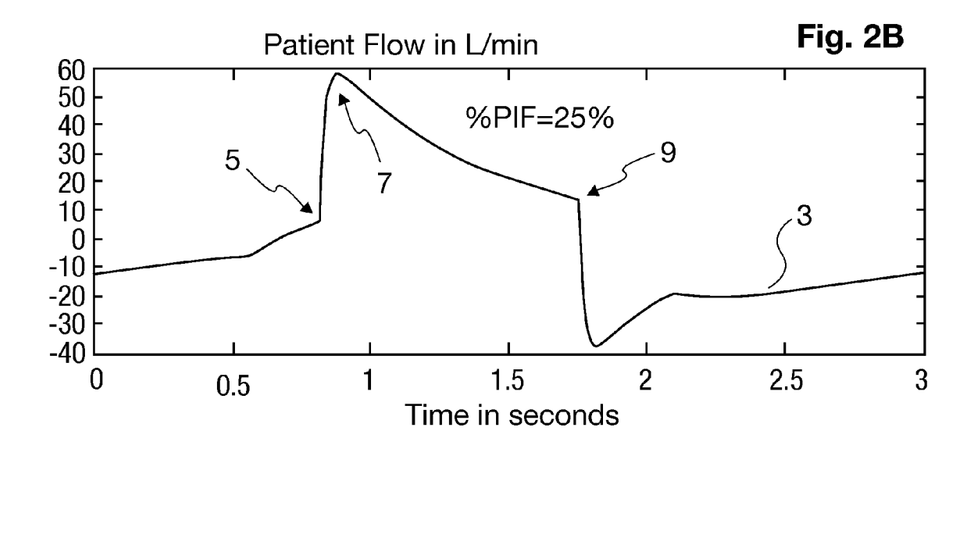
FIG. 2B is a patient flow (in L/min) versus time (in seconds) graph showing an example of respiration with respiration strokes supported during the inspiration.

It is expressly pointed out that the above-described interruption criterion (PEF criterion) can be applied not only to the APRV mode to interrupt an expiratory gas flow, but also to inspiratory respiration processes, such as supporting respiration strokes, for example, as a pressure support (PS) or proportional pressure support (PPS). Supporting respiration strokes are mostly pressure-controlled respiration strokes, which the patient can start (trigger) and end by the patient's spontaneous breathing. The patient (human or animal) is supported in the patient's inspiratory effort by the additional effort of the respirator. However, the inspiration process is interrupted as soon as the inspiratory flow generated by the patient drops below a fixed or settable percentage % PIF (PIF—peak inspiratory flow) of the maximum inspiratory flow. A corresponding example is shown in FIGS. 2A and 2B.

The measured respiratory flow may be a patient flow measured in liters per minute (L/minute), and the corresponding peak respiratory flow may be the maximum intensity of this respiratory flow. The respiratory flow as well as the peak respiratory flow may be both inspiratory and expiratory in nature.

The percentage of the peak respiratory flow set on the device is defined, for example, as a percentage of the peak respiratory flow, so that the portion can be set and expressed as a percentage. However, the percentage may also be expressed in fractions, for example, ½ or ¼ of the peak respiratory flow. The present invention is not limited to the case in which the set percentage must indeed be set manually by the physician or the patient's care provider on the device. Cases in which the percentage of the peak respiratory flow is preset, for example, by the manufacturer, are likewise covered by the present invention, as it can be recognized by the person skilled in the art.

A second step of the process according to the present invention provides for the measurement of the respiratory flow at a second point in time. The measurement may be carried out in any manner that is known and appears to be suitable to the person skilled in the art.

Using the result of measurement, an actual percentage of the respiratory flow measured at the second point in time can be calculated in the process according to the present invention relative to the peak respiratory flow. The respiratory flow measured at the second point in time is related for this purpose to the peak respiratory flow and a corresponding ratio of the two values is calculated as a percentage or fraction or the like. The peak respiratory flow used as the basis herefor may have been determined in the same breathing cycle (where the breathing cycle may be measured, for example, between the beginning of an expiration and the beginning of the next expiration), but it is also possible to use a peak respiratory flow of another breathing cycle taking place at a preceding point in time. It is also possible to use a respiratory flow averaged over a plurality of breathing cycles here.

Furthermore, the actual percentage is regulated to the percentage set on the device when the process according to the present invention is carried out. It is recognizable to the person skilled in the art here that regulation of the set percentage to the actual percentage is also covered by the process according to the present invention.

Thus, it is possible according to the present invention, for the first time ever, to be sure that the respiration process to be initiated will indeed be initiated at a point in time at which the percentage of the peak respiratory flow set on the device also corresponds to the actual percentage. In other words, the physician or the patient's care provider can be sure that the respiration process to be initiated will be initiated exactly at the point in time that the physician or the patient's care provider had intended by setting the percentage on the device. Depending on the respiration system being used and the inertia of that system, it may be necessary for this to wait until the end of a short regulation period. Too extensive an emptying of the gas from the lungs or too late an interruption of an inspiration process—as this may happen, for example, when the above-described process according to the state of the art described in US 2006/0174884 A1 is used—is thus advantageously prevented from occurring according to the present invention. The risk that individual alveoli will collapse in themselves because of the gas being emptied from the lungs too extensively and can be opened again by means of special recruitment maneuvers only, which implies an inevitable stress for the patient, is likewise advantageously avoided.

Thus, the actual percentage of the peak respiratory flow is regulated in a preferred embodiment of the present invention to the set percentage by bringing forward the point in time at which the respiration process is initiated to a third point in time such that the effect of the respiration process begins already at the first point in time. In other words, a delay time of the system between the start or initiation of the respiration process and the onset of the effect of the initiated respiration process is determined, and the point in time at which the respiration process is initiated is brought forward in time by this delay time in further respiration cycles. This embodiment according to the present invention also covers such a regulation whose goal is not to bring forward the point in time at which the respiration process is initiated at a single time, but in which it is necessary to pass through a plurality of loops or cycles to reach the goal of the regulation.

Other, likewise preferred embodiments are advantageously characterized in that a deviation is filtered and/or limited; that a control offset is calculated as the sum of a control offset of an earlier point in time and the deviation, and that the percentage of the control offset to be used is calculated as the sum of the set percentage and the control offset.

This object is also accomplished by the anesthesia device and/or respirator having the features according to the invention. Advantageous variants of the anesthesia device and/or respirator according to the present invention are described herein. Since all the advantages discussed above can be achieved to the full extent by means of the anesthesia device and/or respirator according to the present invention, reference is explicitly made here to the above discussion of these advantages to avoid repetition. Thus, a device having means for carrying out the process according to the present invention is proposed according to the present invention.

The present invention will be explained in detail on the basis of an example with reference to the attached drawings. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Referring to the drawings in particular, FIGS. 1A and 1B show an example of a respiration in the APRV mode in a simulation, where FIG. 1A shows the airway pressure 1 in mbar, FIG. 1B shows the corresponding patient flow 3 in L/minute, in each case over time. The airway pressure 1 varies here between an upper pressure level $P_{high}$ and a lower pressure level $P_{low}$. The pressure level $P_{high}$ is applied here over a duration $T_{high}$, and the lower pressure level $P_{low}$ over a duration $T_{low}$. One of three pressure release phases are marked by arrows in the view in FIG. 1A.

FIGS. 2A and 2B show the simulation of a form of respiration in which the patient is machine-supported by an additional pressure during the spontaneous inspiration. The view in FIG. 2A shows again the airway pressure 1 in mbar, and FIG. 2B shows the patient flow 3 in L/minute, both over time. FIG. 2B shows the starting point 5 of a mechanical inspiration, triggered by the spontaneous effort of the patient, as well as the maximum flow 7 at the level of 58 L/minute. In addition, it can be determined that the % PIF criterion is met at a point in time 9 between 1.5 and 2 sec, % PIF being set at 25% of the maximum flow 7.

Figure 3:
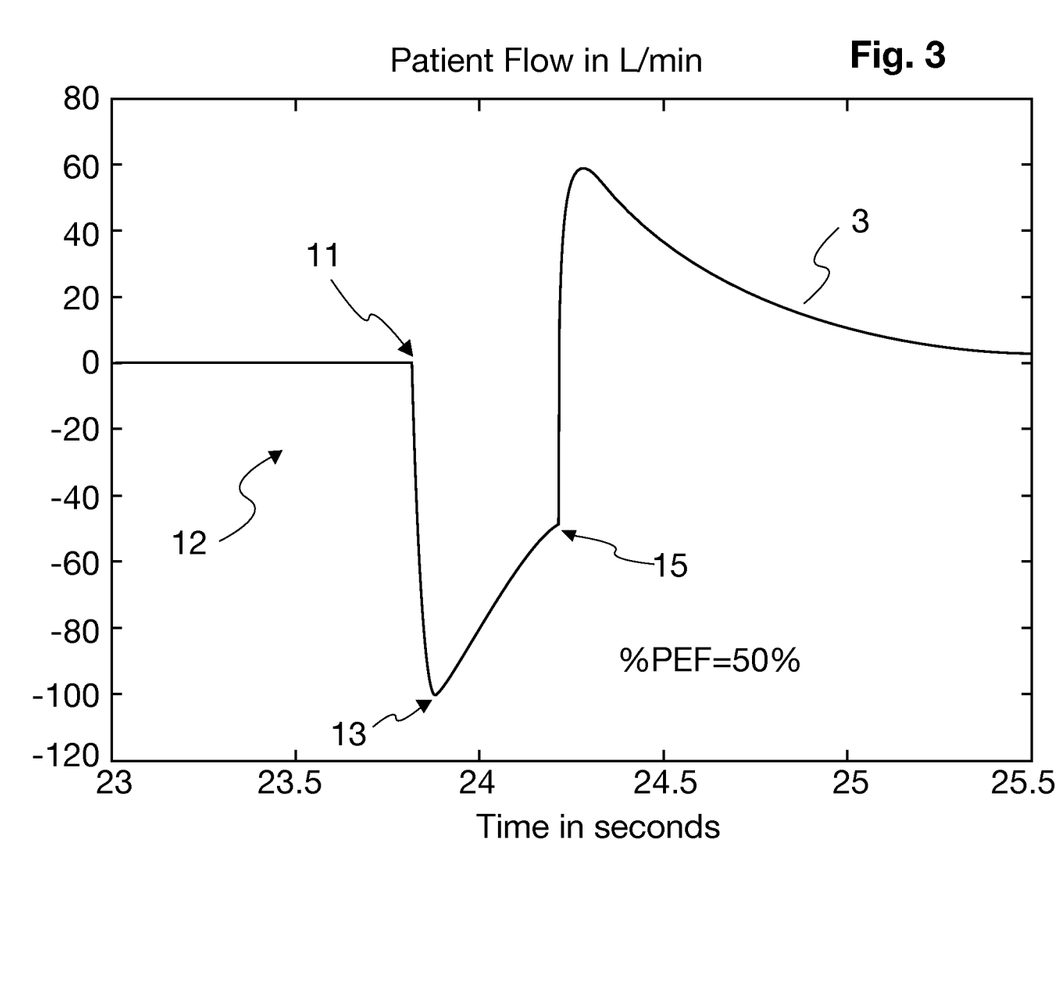
FIG. 3 is a patient flow (in L/min) versus time (in seconds) graph showing a respiration scheme in the APRV mode with a % PEF criterion.

FIG. 3 shows the patient flow 3 over time in a simulation of an APRV respiration. FIG. 3 shows a point in time 11, at which a pressure release phase 12 is started. FIG. 3 shows, furthermore, a point in time 13, at which a maximum flow, which equals 100 L/minute in this case, is reached. In addition, FIG. 3 shows a point in time 15, at which the pressure release phase 12 is interrupted at a set % PEF of 50%.

Figure 4:
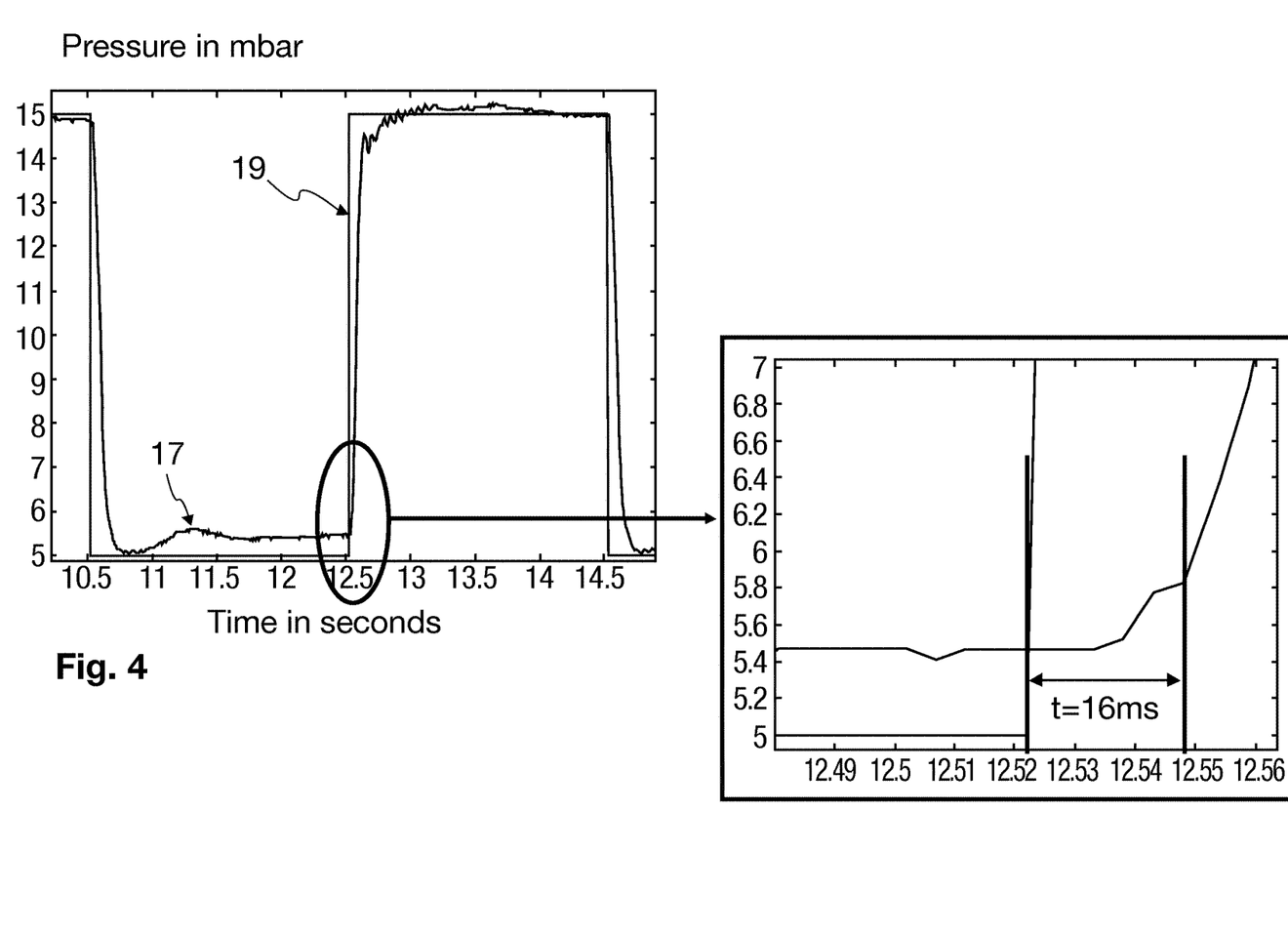
FIG. 4 is a pressure (in mbar) versus time (in seconds) graph showing a procedure for determining a delay time.

FIG. 4 schematically shows a preferred exemplary embodiment of the process according to the present invention. The determination of the delay time is performed with respect to FIG. 4 as follows. The fan of a respirator is operated in a pressure-controlled mode, in which the pressure is switched to and fro between, for example, 5 mbar and 15 mbar. The measured time between the start of inspiration, at which the pressure set point of 5 mbar is raised to 15 mbar, and the actual increase in the airway pressure beyond an existing sensor noise corresponds to the delay time being sought in this exemplary embodiment. As can be determined from the enlargement of the detail marked by an ellipse in FIG. 4, this delay time equals 16 msec in this example, the course of the airway pressure being designated by reference number 17 and the course of the pressure set point by 19 in FIG. 4.

The delay time may be determined at one or more points of the pressure curve and at one or more points of the device. It may be determined, furthermore, on a plurality of devices of the same type, and the mean value can be determined for this plurality of devices. A delay time determined in this manner can thus be assumed to be constant for these purposes.

Figure 5:
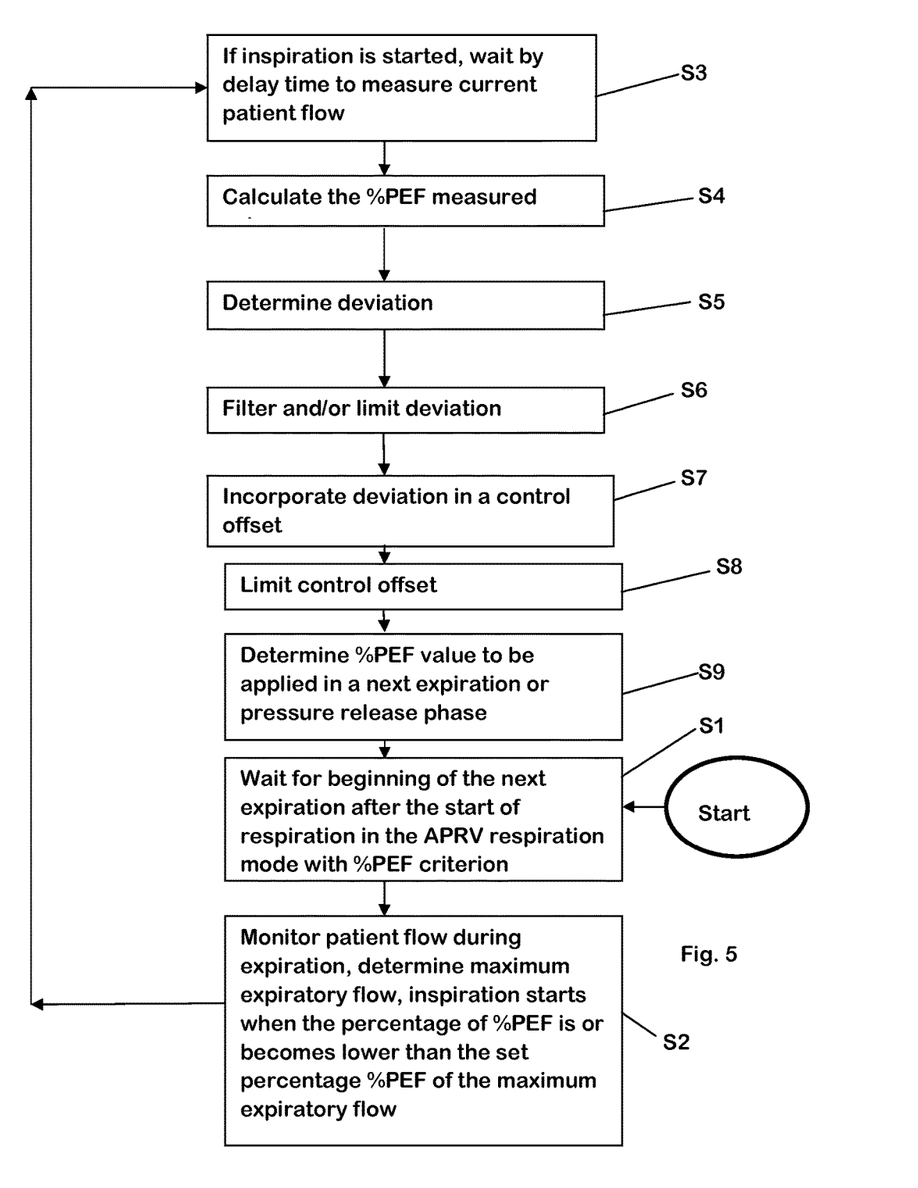
FIG. 5 is a flow diagram showing an exemplary regulation with the % PEF criterion according to the process according to the present invention.

The control circuit, which will be described below, is shown in FIG. 5 and will be explained below, can be designed based on the delay time determined in this manner.

In a step S1, one waits at first for the beginning of the next expiration after the start of respiration in the APRV respiration mode with % PEF criterion.

In a subsequent step S2, the patient flow is monitored during the expiration, the maximum expiratory flow is determined, and inspiration is finally started when the percentage % PEF of the expiratory flow of the patient, measured by the maximum expiratory flow, is or becomes lower than the set percentage % PEF of the maximum expiratory flow (PEF).

If inspiration is started, one waits in step S3 by the delay time in order to measure the current patient flow subsequent thereto in a step S4 and to calculate the % PEF measured value herefrom. The % PEF measured value is obtained from $$\% \text{ PEF measured value} = \frac{\text{current patient flow} \times 100}{\text{maximum expiratory flow}}.$$

A deviation determined in a step S5 is then obtained from the difference between the % PEF set and the measured % PEF measured value:

$$\text{Deviation} = \% \text{ PEF}_{set} - \% \text{ PEF}_{measured}.$$

To avoid fluctuations and to maintain or achieve a smooth system, the deviation can be filtered and/or limited in a step S6 in order to determine or adapt the point in time of the changeover between expiration (pressure release) and inspiration. In particular, it may prove advantageous to use only part of the deviation. In the simplest case, the deviation can be divided for this purpose by a factor, for example, 4. However, more complex filtration is possible as well. The value obtained for the deviation can be subsequently also limited to a maximum increment (a maximum allowable change between two consecutive respiration cycles). This advantageously also contributes to a smooth stabilization and leads to reduced effect of artifacts that may possibly be present and have been generated, for example, by sensor errors, calibration errors, coughing of the patient, handling on the respirator and the like.

The deviation does not change the % PEF value directly, but it becomes incorporated, in a step S7, in a control offset, which represents the sum of the calculated deviations. The control offset is obtained from:

$$\text{Control offset}_{new} = \text{control offset}_{old} + \text{deviation}_{filtered \text{ and } limited}.$$

The control offset can also be limited for safety reasons in a step S8. The regulation thus remains in a working range intended herefor.

The % PEF value to be applied in a next expiration or pressure release phase can finally be determined in a step S9 as follows:

$$\% \text{ PEF}_{applied} = \% \text{ PEF}_{set} + \text{control offset}_{new\_limited}.$$

After conclusion of the pressure release phase, the procedure shown in FIG. 5 can start anew.

By limiting the change in the deviation, overshooting reactions of the regulation are prevented from occurring. To arrive at regulation results in a short time in case of actually desired, pronounced changes—for example, after the start of the processing mode or due to changes made by the user in the setting of the % PEF value—it is also possible to use other filter constants for filtering the deviation, at least temporarily. Thus, it is also possible for the entire deviation to be incorporated in the further process instead of only one fourth of the deviation. Regardless herefrom, a greater, maximum increment may also be allowed for the change in the deviation. The original limitation and/or filtering can be reactivated after the adaptation of the controlled variable (for example, of the % PEF measured value).

To increase the robustness of the process according to the present invention against disturbances, which are due to the patient, for example, caused by poor or no synchronization with the patient, it can be checked when calculating the % PEF measured value whether the measured patient flow and the maximum expiratory flow determined are in an expected window. This is not the case, for example, when the expiratory flow is markedly greater after the end of the delay time after the start of inspiration than immediately at the point in time at which inspiration starts, or when the maximum expiratory flow has not exceeded a minimum, predetermined value of, for example, 1 L/minute. The % PEF measured value is not calculated in such a case and the regulation algorithm is not run. The % PEF value used last is used, instead, in the next phase of expiration. Even if the expiration was not terminated by the % PEF criterion but by the expiration of a maximum time set by the user, the regulation algorithm is not run through again; the % PEF used last continues to be used, rather.

The explanations given here also apply, after a corresponding modification, as can be recognized by the person skilled in the art, to the % PIF criterion mentioned above as well as to all other similar applications.

Figure 6:
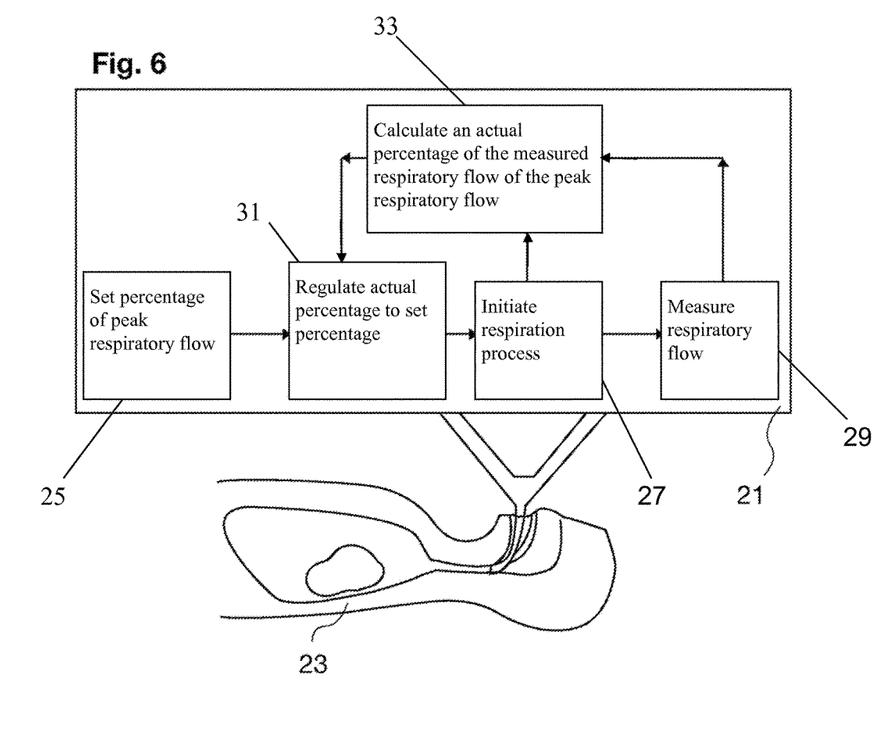
FIG. 6 is a simplified exemplary view of a respirator according to the present invention.

FIG. 6 shows a schematically simplified respirator and/or anesthesia device 21 according to the present invention for respirating a patient 23. The device 21 has a means 25 for setting a percentage of a peak respiratory flow, a means 27 for initiating a respiration process when the set percentage of the peak respiratory flow has been reached and a means 29 for measuring the respiratory flow. The means 33 is intended in this exemplary embodiment according to the present invention for calculating an actual percentage of the measured respiratory flow of the peak respiratory flow. The device 21 has, moreover, a means 31 for regulating the actual percentage determined by the means 33 to the set percentage.

The following procedure is another possibility of accomplishing the object according to the present invention. The applicant reserves the right to also formulate a patent application for a process described below:

The airway pressure ($P_{aw}$) can also be analyzed to measure the % PEF value. A rise in $P_{aw}$ can be interpreted as a reaction to the fact that the % PEF criterion has been reached and to the transition from the low to the high pressure level in case of APRV respiration. Since the pressure rise is known, the patient flow can be measured or taken at a point in time at which $P_{aw}$ has exceeded, for example, 5% of the preset pressure rise:

$$P_{aw} \geq (P_{high} - P_{low}) * 5\% + P_{low}.$$

The patient flow taken at this point in time can be used together with the maximum expiratory flow of the preceding $P_{low}$ phase to determine the % PEF measured value as follows:

$$\% \text{ PEF measured value} = \frac{\text{current patient flow} \times 100}{\text{maximum expiratory flow}}.$$

A patient flow of a preceding point in time (for example, before 15 msec) can also be used in this formulation when the pressure limit is exceeded. The patient flow could also be analyzed, for example, by analyzing the course of the airway pressure curve with known mathematical functions (for example, with the use of the change in slope). The point in time at which the patient flow can be taken can be determined from the analysis of the airway pressures.

These formulations lead to concrete results especially when the time period for the rise of the pressure set point from $P_{low}$ to $P_{high}$ can be approximated with 0 sec.

Furthermore, the patient flow can also be analyzed directly to measure the % PEF value and the actual point in time at which the transition from $P_{low}$ to $P_{high}$ is accomplished can be determined with mathematical functions.

Thus, the present invention proposes, for the first time ever, a process for operating a respirator and/or anesthesia device with measurement of a % PEF or % PIF to be set and with regulation of the measured % PEF or % PIF to the set % PEF or % PIF. Furthermore, the present invention shows a suitable respirator and/or anesthesia device.

While specific embodiments of the invention have been shown and described in detail to illustrate the application of the principles of the invention, it will be understood that the invention may be embodied otherwise without departing from such principles.

What is claimed is:

1. A process for operating a respirator device and/or an anesthesia device, the process comprising the steps of:
    setting a percentage of a peak respiratory flow on the respirator and/or anesthesia device;
    initializing an automated airway pressure release respiration process at a first point in time, at which a measured respiratory flow reaches said percentage of said peak respiratory flow set on the device;
    providing at least a pressure release associated with said automated airway pressure release respiration process at a second point in time that is after the first point in time;
    measuring respiratory flow at the second point in time;
    calculating an actual percentage of said respiratory flow measured at the second point in time relative to said peak respiratory flow;
    continuously determining a delay between said initialization of said automated airway pressure release respiration process and said pressure release of said automated airway pressure release respiration process during one or more cycles of said automated airway pressure release respiration process, said pressure release corresponding to a change in pressure in a flow of fluid from a first pressure to a second pressure, said first pressure being greater than said second pressure; and continuously regulating the actual percentage of respiratory flow to the set percentage of respiratory flow or regulating the set percentage of respiratory flow to the actual percentage of respiratory flow, wherein said regulation is achieved by initiating one or more further cycles of said automated airway pressure release respiration process based on said delay, wherein said pressure release associated with said automated airway pressure release respiration process begins at one of an earlier point in time and a later point in time in said one or more further cycles of said automated airway pressure release respiration process.

2. A process in accordance with claim 1, further comprising: determining whether said measured respiratory flow at the second point in time is within an expected window, wherein said actual percentage of said respiratory flow is not calculated if said measured respiratory flow at the second point in time is not within said expected window, wherein said actual percentage of respiratory flow is determined based on at least said respiratory flow measured at the second point in time and said peak respiratory flow, said initialization of said automated airway pressure release respiration process comprising a transition from a first phase of respiration into a second phase of respiration, said first phase of respiration being different from said second phase of respiration.

3. A process in accordance with claim 1, further comprising calculating a deviation between the actual percentage of respiratory flow and the set percentage of respiratory flow, wherein said delay is compensated for in a second cycle of said automated airway pressure release respiration process.

4. A process in accordance with claim 3, further comprising filtering and/or limiting the deviation between the actual percentage of respiratory flow and the set percentage of respiratory flow.

5. A process in accordance with claim 3, further comprising calculating a control offset as a sum of a control offset of an earlier point in time and the deviation between the actual percentage of respiratory flow and the set percentage of respiratory flow.

6. A process in accordance with claim 5, further comprising filtering and/or limiting the control offset.

7. A process in accordance with claim 6, further comprising calculating of a percentage to be applied as a sum of said set percentage of respiratory flow and of said control offset.

8. A process in accordance with claim 1, wherein said step of regulating compensates for said delay between an onset of said pressure release and the initialization of said airway pressure release respiration process during said second cycle of said airway pressure release respiration process, said airway pressure release respiration process comprising a transition from a first phase of respiration into a second phase of respiration, said first phase of respiration being different from said second phase of respiration.

9. A process for operating a respirator device and/or an anesthesia device, the process comprising the steps of:

providing a respirator device and/or an anesthesia device, wherein a flow of fluid is provided to a patient via said respirator device and/or said anesthesia device;

setting a percentage of a peak expiratory flow on the respirator and/or the anesthesia device;

initializing a respiration process at a first point in time such that a pressure release associated with said respiration process occurs at a second point in time, said pressure release corresponding to a change in pressure of said flow of fluid from a first pressure to a second pressure, said first pressure being greater than said second pressure;

measuring an amount of said pressure release;

determining an actual percentage of the peak expiratory flow based on said measured amount of said pressure release in one or more cycles of said respiration process;

determining a delay between said initialization of said respiration process and said pressure release; and regulating the actual percentage of the peak expiratory flow to the set percentage of the peak expiratory flow when said actual percentage of the peak expiratory flow is not equal to said set percentage of the peak expiratory flow based on said delay by adjusting a timing of said pressure release in another cycle of said respiration process such that said actual percentage of the peak expiratory flow reaches said percentage of the peak expiratory flow set on the device in the another cycle of said respiration process.

10. A process in accordance with claim 9, further comprising;

calculating a deviation between the actual percentage of respiratory flow and the set percentage of respiratory flow;

measuring a patient flow and a maximum expiratory flow;

determining whether said patient flow and said maximum expiratory flow are within a predetermined range, wherein said actual percentage of said respiratory flow is not calculated when said patient flow and said maximum expiratory flow are not within said predetermined range.

11. A process in accordance with claim 10, further comprising filtering and/or limiting the deviation between the actual percentage of respiratory flow and the set percentage of respiratory flow.

12. A process in accordance with claim 10, further comprising calculating a control offset as a sum of a control offset of an earlier point in time and the deviation between the actual percentage of respiratory flow and the set percentage of respiratory flow.

13. A process in accordance with claim 12, further comprising filtering and/or limiting the control offset.

14. A process in accordance with claim 9, wherein said step of regulating compensates for said time delay between an onset of said pressure release and the initialization of said respiration process during said another cycle of said respiration process, said respiration process comprising a transition from a first phase of respiration into a second phase of respiration, said first phase of respiration being different from said second phase of respiration.

* * * * *